United States Patent [19]

Kurauchi et al.

[11] Patent Number: 5,292,925
[45] Date of Patent: Mar. 8, 1994

[54] N-T-BUTYLOXYCARBONYL-3-CYCLOHEXYL-L-ALANINE METHYL ESTER IN CRYSTALLINE FORM

[75] Inventors: Masahiko Kurauchi; Tohru Nakamura, both of Kawasaki, Japan

[73] Assignee: Ajinomoto Co., Inc., Tokyo, Japan

[21] Appl. No.: 13,990

[22] Filed: Feb. 5, 1993

Related U.S. Application Data

[63] Continuation of Ser. No. 813,692, Dec. 27, 1991, abandoned.

Foreign Application Priority Data

Dec. 28, 1990 [JP] Japan .................................. 2-418803

[51] Int. Cl.$^5$ .......................................... C07C 261/00
[52] U.S. Cl. ...................................................... 560/115
[58] Field of Search ......................................... 560/115

[56] References Cited

U.S. PATENT DOCUMENTS 5,010,057  4/1991  Henning ............................ 530/330

OTHER PUBLICATIONS

Ault, "Techniques and Experiments for Organic Chemistry," 4th Ed, pp. 56–57 (1983) Bayer, J. Med. Chem., 28 pp. 1779–1790 (1985).

Primary Examiner—Michael L. Shippen
Attorney, Agent, or Firm—Oblon, Spivak, McClelland, Maier & Neustadt

[57] ABSTRACT

N-t-butyloxycarbonyl-3-cyclohexyl-L-alanine methyl ester, previously known only as an oil, is provided in crystalline form. By addition of an organic solvent, such as methanol and/or n-hexane, to the ester in the form of an oil and cooling, crystals may be obtained. Alternatively, the ester in oily form may be seeded with a crystal produced previously. The crystalline material is of higher purity than the previously known oils, and is more useful than the oils as an intermediate in the pharmaceutical industry.

1 Claim, 2 Drawing Sheets

N-T-BUTYLOXYCARBONYL-3-CYCLOHEXYL-L-ALANINE METHYL ESTER IN CRYSTALLINE FORM

This application is a continuation of application Ser. No. 07/813,692, filed on Dec. 27, 1991, now abandoned.

BACKGROUND OF THE INVENTION

1. Field of the Invention

The present invention relates to crystals of N-t-butyloxycarbonyl-3-cyclohexyl-L-alanine methyl ester, an important intermediate in the manufacture of pharmaceuticals, and a method of producing the same.

2. Discussion of the Background

N-t-butyloxycarbonyl-3-cyclohexyl-L-alanine methyl ester has the following formula (1):

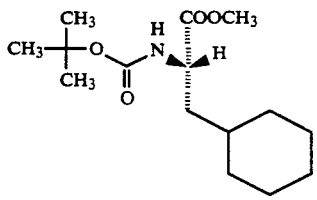

N-t-butyloxycarbonyl-3-cyclohexyl-L-alanine methyl ester is important as an intermediate in the production of various pharmaceuticals.

N-t-butyloxycarbonyl-3-cyclohexyl-L-alanine methyl ester can be synthesized by the method disclosed by Boger et al (J. Med. Chem., 28, 1779 (1985)), but is obtained as an oily substance. There have been no reports of this compound being obtained in the form of crystals.

It is desirable to produce crystals of N-t-butyloxycarbonyl-3-cyclohexyl-L-alanine methyl ester since crystals generally have a higher purity than the corresponding oil, and thus, are better suited to use as an intermediate in the pharmaceutical industry. Furthermore, crystals are easier to transport and handle than the corresponding oils.

SUMMARY OF THE INVENTION

Accordingly, one object of the present invention is to provide N-t-butyloxycarbonyl-3-cyclohexyl-L-alanine methyl ester of the formula (1) in crystalline form:

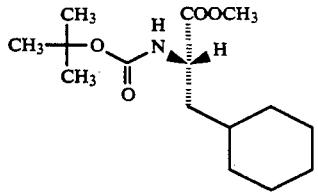

Another object of the present invention is to provide a method for the production of crystalline N-t-butyloxycarbonyl-3-cyclohexyl-L-alanine methyl ester, comprising adding an organic solvent to said ester in oily form.

Another object of the present invention is to provide a method for the production of crystalline N-t-butyloxycarbonyl-3-cyclohexyl-L-alanine methyl ester, comprising adding a seed crystal of N-t-butyloxycarbonyl-3-cyclohexyl-L-alanine methyl ester to oily N-t-butyloxycarbonyl-3-cyclohexyl-L-alanine methyl ester.

These and other objects which will become apparent during the following detailed description are provided by adding an organic solvent, such as a hydrocarbon solvent (e.g., n-hexane) and/or a lower alcohol (e.g., methanol) to the oily N-t-butyloxycarbonyl-3-cyclohexyl-L-alanine methyl ester, resulting in the formation of crystals.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
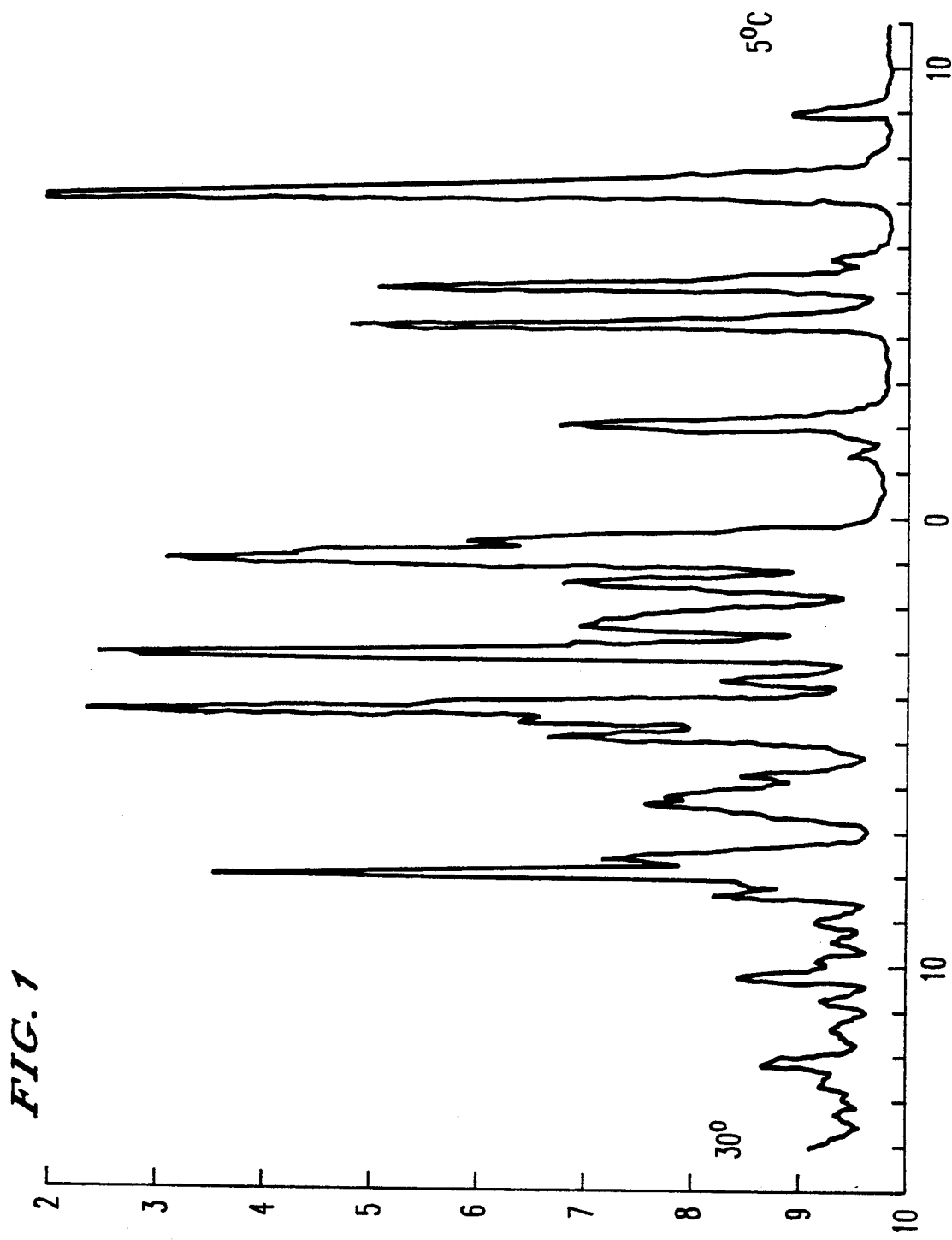
FIG. 1 shows a powder X-ray chart of the crystals prepared in Example 1 below.
Figure 2:
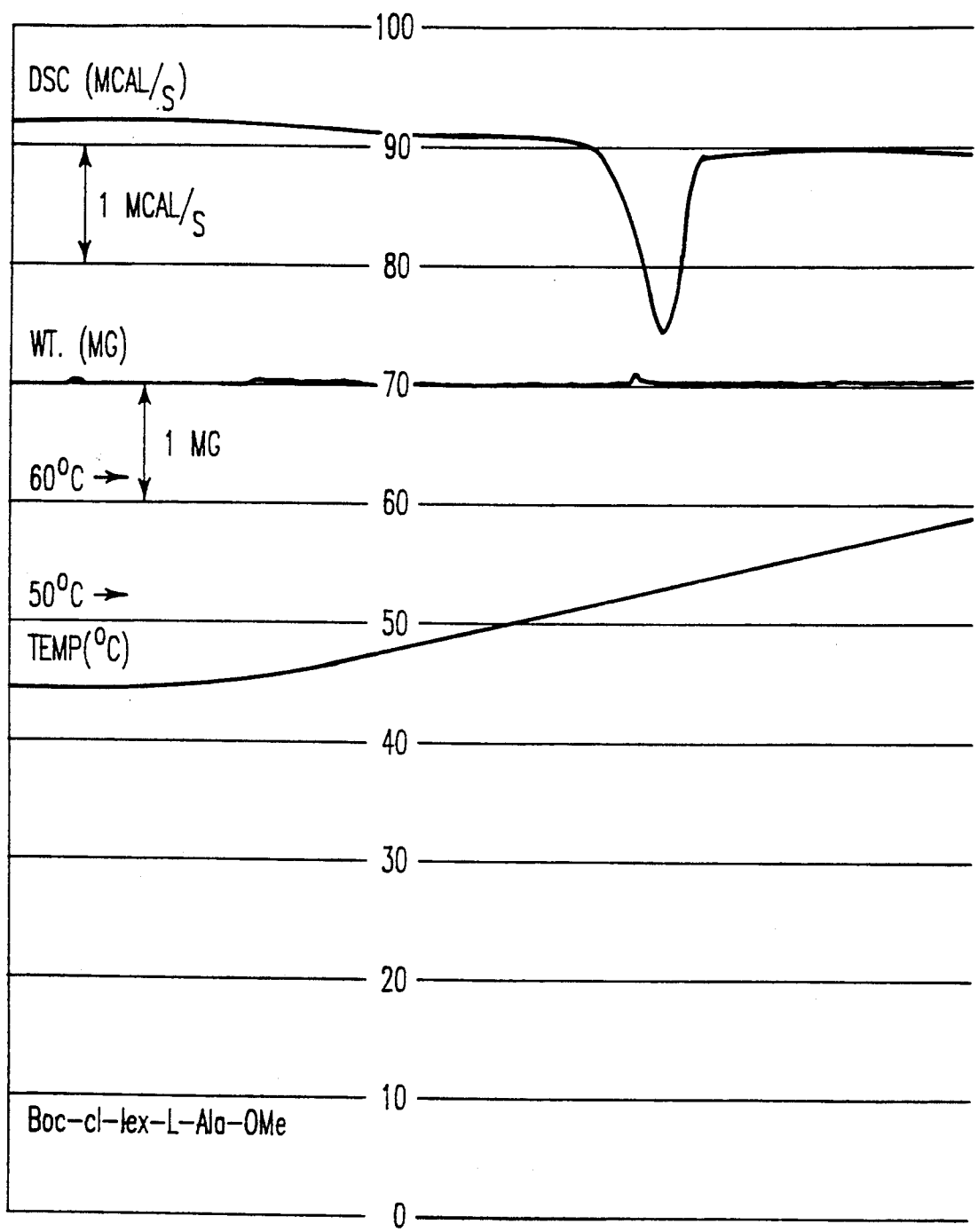
FIG. 2 shows a DSC chart of the crystals prepared in Example 1.

The crystals can, for example, be obtained by adding n-hexane and/or methanol to the oily N-t-butyloxycarbonyl-3-cyclohexyl-L-alanine. In addition to methanol, suitable lower alcohol solvents include ethanol and/or isopropyl alcohol, and in addition to n-hexane, suitable hydrocarbon solvents include cyclohexane and petroleum ether, which can be either low-boiling (30°-60° C.) or high-boiling (ligroin or petroleum benzin). Preferred solvents are n-hexane, methanol and mixtures thereof.

Preferably, the mixture of oily ester and organic solvent is subsequently cooled; for example, from a temperature of above 20° C. to a temperature about or below 20° C. Crystals produced previously may be used to seed the mixture of ester and solvent. More preferably, the addition of the organic solvent or organic solvent mixture takes place at a temperature of 20° C. or above, particularly preferably from greater than 20° C. to 50° C., and is followed by cooling to 20° C. or below, particularly preferably from 0° C. to 20° C.

When only n-hexane is used, from 0 to 50 wt %, preferably 25 to 40 wt %, of n-hexane to N-t-butyloxycarbonyl-3-cyclohexyl-L-alanine is added. When only methanol is used, from 0 to 35 wt %, preferably 15 to 25 wt %, of methanol is added. When a mixture of n-hexane and methanol is used, from 0 to 40 wt %, preferably 3 to 30 wt %, of n-hexane and from 0 to 25 wt %, preferably 1 to 15 wt %, of methanol is used.

As an alternative to the use of solvent, a method for the production of the compound of formula (1) in crystalline form comprises adding to the ester in oily form one or more seed crystals. These crystals may have been previously produced by the use of an organic solvent by a method according to the present invention described above.

N-t-butyloxycarbonyl-3-cyclohexyl-L-alanine methyl ester can be prepared by reacting, for example, L-phenylalanine methyl ester hydrochloride with di-t-butyl dicarbonate in the presence of, for example, triethylamine and reducing the resulting N-t-butyloxycarbonyl-L-phenylalanine methyl ester with hydrogen in methanol in the presence of a rhodium catalyst.

Other features of the invention will become apparent in the course of the following descriptions of exemplary embodiments which are given for illustration of the invention and are not intended to be limiting thereof.

EXAMPLES

Embodiments of the present invention are described below by way of example only.

EXAMPLE 1

After 13.0 ml (6.8 wt %) of n-hexane and 40 ml (2.6 wt %) of methanol were added to 126 g of oily N-t-butyloxycarbonyl-3-cyclohexyl-L-alanine methyl ester at room temperature (about 25° C.), the mixture was cooled to 4° C. while stirring. The precipitated crystals were immediately separated by centrifuging, and were then washed with 7 ml of previously cooled n-hexane. After the obtained crystals were air-dried, the crystals were further dried at 30° C. overnight under reduced pressure to give 3.7 g of N-t-butyloxycarbonyl-3-cyclohexyl-L-alanine methyl ester as crystals.

The crystals were subjected to a variety of analytical tests as specified below. The powder X-ray chart of the crystals is shown in FIG. 1.

$^1$H-NMR (CDCl$_3$): $\delta = 4.87$ (d, 1H), 4.32 (d, 1H), 3.72 (s, 3H), 1.81 (d, 1H), 1.66 (m, 6H), 1.43 (s, 9H), 1.33 (m, 1H), 1.18 (m, 3H), 0.92 (m, 2H)

Mass spectrum (FAB): 286 (M+)

Specific rotation (20° C., C=1, methanol): $-20.0°$

Melting point: 48.9°–49.2° C.

EXAMPLE 2

After 9.3 ml (9.9 wt %) of n-hexane and 4.7 ml (6.2 wt %) of methanol were added to 62 g of oily N-t-butyloxycarbonyl-3-cyclohexyl L-alanine methyl ester at room temperature (about 25° C.), the mixture was gradually cooled while stirring. When the temperature of the liquid reached 15° C., crystals of N-t-butyloxycarbonyl-3-cyclohexyl-L-alanine methyl ester (0.1 g) prepared in Example 1 were added as seed crystals. Cooling was further continued while stirring until the temperature reached 4° C. The precipitated crystals were immediately separated by centrifuging and were then washed with 3 ml of previously cooled n-hexane. After the obtained crystals were air-dried, the crystals were further dried at 30° C. overnight under reduced pressure to give 28.5 g of N-t-butyloxycarbonyl-3-cyclohexyl-L-alanine methyl ester as crystals.

EXAMPLE 3

After 25.0 ml (19.8 wt %) of methanol was added to 100 g of oily N-t-butyloxycarbonyl-3-cyclohexyl-L-alanine at room temperature (about 25° C.), the mixture was gradually cooled while stirring. When the temperature of liquid reached 13° C. crystals of N-t-butyloxycarbonyl-3-cyclohexyl-L-alanine methyl ester (1.0 g) prepared in Example 1 were added as seed crystals. Cooling was continued to 12° C. while stirring. The precipitated crystals were immediately separated by centrifuging, and were then washed with 5 ml of previously cooled methanol. After the obtained crystals were air-dried, the crystals were further dried at 30° C. overnight under reduced pressure to give 71.2 g g of N-t-butyloxycarbonyl-3-cyclohexyl-L-alanine methyl ester as crystals.

EXAMPLE 4

After 50.0 ml (33.0 wt %) of n-hexane was added to 100 g of oily N-t-butyloxycarbonyl-3-cyclohexyl-L-alanine at room temperature (about 25° C.), the mixture was gradually cooled while stirring. When the temperature of liquid reached 22°0 C., crystals of N-t-butyloxycarbonyl-3-cyclohexyl-L-alanine methyl ester (1.0 g) prepared in Example 1 were added as seed crystals. Cooling was continued to 20° C. while stirring. The precipitated crystals were immediately separated by centrifuging, and were then washed with 5 ml of previously cooled n-hexane. After the obtained crystals were air-dried, the crystals were further dried at 30° C. overnight under reduced pressure to give 79.9 g of N-t-butyloxycarbonyl-3-cyclohexyl-L-alanine methyl ester as crystals.

EXAMPLE 5

After 25.0 ml (19.8 wt %) of methanol was added to 100 g of oily N-t-butyloxycarbonyl-3-cyclohexyl-L-alanine at room temperature (about 25° C.), the mixture was heated to 40° C. while stirring. When the temperature of liquid reached 40° C., methanol was evaporated under reduced pressure. Oily N-t-butyloxycarbonyl-3-cyclohexyl-L-alanine methyl ester was again obtained. Crystals of N-t-butyloxycarbonyl-3-cyclohexyl-L-alanine methyl ester prepared in Example 1 (1.0 g) were added to the oil as seed crystals. Cooling was gradually continued to 15° C. while stirring. The precipitated crystals were immediately separated by centrifuging, and were then washed with 5 ml of previously cooled methanol. After the obtained crystals were air-dried, the crystals were further dried at 30° C. overnight under reduced pressure to give 84.3 g of N-t-butyloxycarbonyl-3-cyclohexyl-L-alanine methyl ester as crystals. The powder X-ray chart for the crystals formed in this way resembled that shown in FIG. 1 for the crystals of Example 1.

Obviously, numerous modifications of the present invention are possible in light of the above teachings. It is therefore to be understood that within the scope of the appended claims, the invention may be practiced otherwise than as specifically described herein.

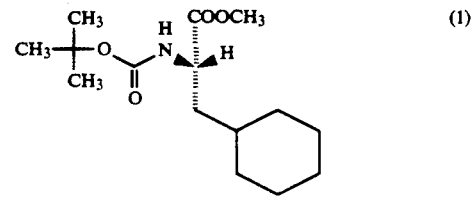

What is claimed as new and desired to be secured by Letters Patent of the United State is:

1. N-t-butyloxycarbonyl-3-cyclohexyl-L-alanine methyl ester of formula (1) in crystalline form: